(12) United States Patent  
Neilson et al.

(10) Patent No.: US 8,202,702 B2
(45) Date of Patent: Jun. 19, 2012

(54) METHOD AND DEVICE FOR MEASURING EXTRACELLULAR ACIDIFICATION AND OXYGEN CONSUMPTION RATE WITH HIGHER PRECISION

(75) Inventors: Andy C. Neilson, Groton, MA (US); Suzanne Armitstead, Bedford, NH (US); Yevgeniy Margolin, Medfield, MA (US); Stephen C. Young, Chicopee, MA (US)

(73) Assignee: Seahorse Bioscience, Billerica, MA (US)

( * ) Notice: Subject to any disclaimer, the term of this patent is extended or adjusted under 35 U.S.C. 154(b) by 299 days.

(21) Appl. No.: 12/579,012

(22) Filed: Oct. 14, 2009

(65) Prior Publication Data

US 2010/0124761 A1 May 20, 2010

Related U.S. Application Data

(60) Provisional application No. 61/105,201, filed on Oct. 14, 2008.

(51) Int. Cl.
*C12Q 1/02* (2006.01)
*C12M 1/34* (2006.01)
*C12M 3/00* (2006.01)

(52) U.S. Cl. ............... 435/29; 435/287.1; 435/287.2; 435/288.3; 435/284.4; 435/287.5

(58) Field of Classification Search ............ 435/29, 435/287.1, 287.2, 288.3, 288.4
See application file for complete search history.

(56) References Cited

U.S. PATENT DOCUMENTS

| | | |
|---|---|---|
| 4,065,357 A | 12/1977 | Groves |
| 4,256,832 A | 3/1981 | Findl et al. |
| 4,461,328 A | 7/1984 | Kenney |
| 4,498,510 A | 2/1985 | Minshew, Jr. et al. |
| 4,599,315 A | 7/1986 | Terasaki et al. |
| 4,711,851 A | 12/1987 | McNamara et al. |
| 4,879,097 A | 11/1989 | Whitehead et al. |
| 5,104,804 A | 4/1992 | Humphries et al. |
| 5,250,419 A | 10/1993 | Bernard et al. |
| 5,278,048 A | 1/1994 | Parce et al. |
| 5,459,300 A | 10/1995 | Kasman |
| 5,468,605 A | 11/1995 | Harris et al. |
| 5,495,850 A | 3/1996 | Zuckerman |
| 5,496,697 A | 3/1996 | Parce et al. |
| 5,536,662 A | 7/1996 | Humphries et al. |
| 5,567,598 A | 10/1996 | Stitt et al. |
| 5,728,541 A | 3/1998 | Kornblith |
| 5,766,875 A | 6/1998 | Hafeman et al. |
| 5,774,214 A | 6/1998 | Prettyjohns |
| 5,792,426 A | 8/1998 | Portmann et al. |
| 5,830,138 A | 11/1998 | Wilson |
| 5,959,297 A | 9/1999 | Weinberg et al. |
| 5,998,517 A | 12/1999 | Gentle, Jr. et al. |
| 6,030,917 A | 2/2000 | Weinberg et al. |
| 6,078,698 A | 6/2000 | Lorton et al. |
| 6,080,574 A | 6/2000 | Berndt |
| 6,083,761 A | 7/2000 | Kedar et al. |
| D438,631 S | 3/2001 | Miller |
| D438,632 S | 3/2001 | Miller |
| D438,633 S | 3/2001 | Miller |
| 6,306,658 B1 | 10/2001 | Turner et al. |
| 6,376,233 B1 | 4/2002 | Wolf et al. |
| 6,380,605 B1 | 4/2002 | Verhaegen |
| 6,395,506 B1 | 5/2002 | Pitner et al. |
| 6,395,555 B1 | 5/2002 | Wilson et al. |
| 6,416,967 B2 | 7/2002 | Kornblith |
| 6,468,736 B2 | 10/2002 | Brooker |
| 6,486,947 B2 | 11/2002 | Modlin et al. |
| 6,627,158 B1 | 9/2003 | Peltier |
| 6,653,124 B1 | 11/2003 | Freeman |
| 6,673,532 B2 | 1/2004 | Rao |
| 6,766,817 B2 | 7/2004 | da Silva |
| 6,821,787 B2 | 11/2004 | Neilson et al. |
| 6,835,574 B2 | 12/2004 | Neilson et al. |
| 6,880,158 B1 | 4/2005 | Basso et al. |
| 6,881,584 B1 | 4/2005 | Lenhard et al. |
| 6,887,680 B2 | 5/2005 | Kornblith |
| 6,900,027 B1 | 5/2005 | Kornblith |
| 6,918,404 B2 | 7/2005 | Dias da Silva |
| 6,933,129 B1 | 8/2005 | Kornblith |
| 7,066,586 B2 | 6/2006 | da Silva |
| 7,276,351 B2 | 10/2007 | Teich et al. |
| 7,638,321 B2 | 12/2009 | Teich et al. |
| 7,795,012 B2 | 9/2010 | Lehmann et al. |
| 7,851,201 B2 | 12/2010 | Teich et al. |
| 2001/0051353 A1 | 12/2001 | Kornblith |
| 2002/0098592 A1 | 7/2002 | Neilson et al. |
| 2002/0098593 A1 | 7/2002 | Nelson et al. |
| 2002/0132360 A1 | 9/2002 | Neilson et al. |
| 2002/0146345 A1 | 10/2002 | Neilson et al. |
| 2002/0146836 A1 | 10/2002 | Neilson et al. |
| 2002/0168679 A1 | 11/2002 | Naus et al. |
| 2002/0192638 A1 | 12/2002 | Kornblith |
| 2003/0059807 A1 | 3/2003 | Roach et al. |
| 2003/0162285 A1 | 8/2003 | Tajima |
| 2004/0023375 A1 | 2/2004 | Kornblith et al. |
| 2004/0072722 A1 | 4/2004 | Kornblith et al. |
| 2004/0077075 A1 | 4/2004 | Jensen et al. |
| 2004/0086888 A1 | 5/2004 | Kornblith et al. |
| 2004/0107986 A1 | 6/2004 | Neilson et al. |
| 2004/0110301 A1 | 6/2004 | Neilson et al. |

(Continued)

FOREIGN PATENT DOCUMENTS

DE 4016617 A1 11/1991

(Continued)

OTHER PUBLICATIONS

Office Action in Chinese Patent Application No. 200780031522.6, dated Feb. 1, 2011.

(Continued)

*Primary Examiner* — Herbert J Lilling
(74) *Attorney, Agent, or Firm* — Goodwin Procter LLP (57) ABSTRACT

The accuracy and/or precision of measurements of extracellular acidification rate or $CO_2$ evolution in cell culture medium may be improved by using materials with low $CO_2$ permeability for medium-containing vessels.

22 Claims, 8 Drawing Sheets

U.S. PATENT DOCUMENTS

| | | | |
|---|---|---|---|
| 2004/0121454 | A1 | 6/2004 | Jury et al. |
| 2004/0197905 | A1 | 10/2004 | Hafeman |
| 2005/0054028 | A1 | 3/2005 | Teich et al. |
| 2007/0037285 | A1 | 2/2007 | Ehret et al. |
| 2008/0014571 | A1 | 1/2008 | Teich et al. |
| 2010/0227385 | A1 | 9/2010 | Teich et al. |

FOREIGN PATENT DOCUMENTS

| | | |
|---|---|---|
| DE | 4217868 A1 | 12/1993 |
| DE | 4405375 A1 | 8/1995 |
| DE | 10136005 C1 | 11/2002 |
| DE | 10329983 A1 | 3/2005 |
| EP | 0363262 A1 | 4/1990 |
| EP | 0722136 A2 | 7/1996 |
| FR | 2792333 A1 | 10/2000 |
| WO | WO-9522406 | 8/1995 |
| WO | WO-9815645 | 4/1998 |
| WO | WO-9955827 | 11/1999 |
| WO | WO-9960630 | 11/1999 |
| WO | WO-0032308 A2 | 6/2000 |
| WO | WO-0036410 A1 | 6/2000 |
| WO | WO-0185901 A2 | 11/2001 |
| WO | WO-0202736 | 1/2002 |
| WO | WO-0208385 | 1/2002 |
| WO | WO-0211881 | 2/2002 |
| WO | WO-02061858 A2 | 8/2002 |
| WO | WO-02072423 A1 | 9/2002 |
| WO | WO-02083852 A2 | 10/2002 |
| WO | WO-02099386 A2 | 12/2002 |
| WO | WO-03000557 A2 | 1/2003 |
| WO | WO-03004596 A1 | 1/2003 |
| WO | WO-03059518 A1 | 7/2003 |
| WO | WO-2004065618 A2 | 8/2004 |
| WO | WO-2004094060 A1 | 11/2004 |

OTHER PUBLICATIONS

"How to Adjust pH Levels," in Office Action mailed Sep. 28, 2010 in U.S. Appl. No. 11/486,440.

Ainscow et al., "Top-down control analysis of ATP turnover, glycolysis and oxidative phosphorylation in rat hepatocytes," Eur. J. Biochem., 263(3):671-85 (Aug. 1999).

Andreescu et al., "Autonomous Multielectrode System for Monitoring the Interations of Isoflavonoids with Lung Cancer Cells," 76 Anal. Chem. 8, pp. 2321-2330 (2004).

Andreescu, S. et al., "Advanced electrochemical sensors for cell cancer monitoring," Methods, vol. 37 pp. 84-93 (2005).

Gatti et al., "Oxygen microoptodes: a new tool for oxygen measurments in aquatic animal ecology," Marine Biology, 2002, 140:1075-1085.

Gump et al., "TAT transduction: the molecular mechanism and therapeutic prospects," Trends Mol. Med., 13(10):443-48 (2007).

Jekabsons et al., "Bioenergetic analysis of cerebellar granule neurons undergoing apoptosis by potassium/serum deprivation," Cell Death Differ. 13(9):1595-610 (Sep. 2006) (Epub Jan. 20, 2006).

Karasinski, J. et al., "Detection and identification of bacteria using antibiotic susceptibility and a multi-array electrochemical sensor with pattern recognition," Biosensors and Bioelectronics, vol. 22, pp. 2643-2649 (2007).

Lou et al., "Mitochondrial uncouplers with an extraordinary dynamic range," Biochem J., 407(1):129-40 (Oct. 2007).

Maharbiz et al., "Silicon microbial bioreactor arrays," Poster 83, 1st Annual International IEEE-EMBS Special Topic Conference on Microtechnologies in Medicine & Biology, Lyon, France, Publ date Oct. 12-14, 2000.

Official Action in European Patent Application No. 04788615.5-1234, dated Sep. 8, 2010, 6 pages.

Office Action in Chinese Patent Application No. 200780031522.6, dated Jul. 15, 2010 (translation).

Scott et al., "Energy transduction in intact synaptosomes. Influence of plasma-membrane depolarization on the respiration and membrane potential of internal mitochondria determined in situ," Biochem. J. 186(1):21-33 (Jan. 1980).

Terada, "Uncouplers of oxidative phosphorylation," Environ. Health Perspect., 87:213-18 (1990).

Van der Gun et al., "Serum insensitive, intranuclear protein delivery by the multipurpose cationic lipid SAINT-2," J. Control Release, 123:228-238 (2007).

Yang et al., "Reversible and repeatable linear local cell force response under large stretches," Experimental Cell Research, Apr. 2005, 305:42-50.

"The Nature of ATP," ATP and Biological Energy, (as printed from Internet on Oct. 4, 2005, http://www.emc.maricopa.edu/faculty/farabee/BIOBK/BioBookATP.html).

Amano et al., "Measuring respiration of cultured cell with oxygen electrode as a metabolic indicator for drug screening," Human Cell 12(1):3-10 (1999).

B. Cunningham, P. Li, B. Lin, J. Pepper, "Colorimetric resonant reflection as a direct biochemical assay technique," Sensors and Actuators B, vol. 81, p. 316-328, Jan. 5, 2002.

Beebe D.J., Mensing G.A., Walker G.M. (2002) "Physics and applications of microfluidics in biology." Annu. Rev. Biomed. Eng., 4, 261-86.

Beebe D.J., et al., (2000) Functional hydrogel structures for autonomous flow control inside microfluidic channels. Nature, 404, 588-90.

Bousse, L., et al., "Electrokinetically Controlled Microfluidic Analysis Systems." Annu. Rev. Biophys. Biomol. Struct. 29, 155-181 (2000).

Brecht & Gauglitz, "Optical probes and transducers," Biosensors and Bioelectronics, 10, p. 923-936, 1995.

Burd et al., "Tumor oxygenation and acidification are increased in melanoma xenografts after exposure to hyperglycemia and meta-iodo-benzylguanidine," Rediation Research 159:328-335 (2003).

Clark, L.C. Jnr. Ann. NY Acad. Sci. 1962; 102:29-45.

Criddle et al. "Simultaneous Measurement of Metabolic Heat Rate, $CO_2$ Production, and $O_2$ Consumption by Microcalorimetry" Analytical Biochem. 1991, 194:413-417.

Deshpande et al., "Microplates with integrated oxygen sensing for medium optimization in animal cell culture," Cytotechnology 46:1-8 (2004).

Ekelund et al., "Microphysiometry: new technology for evaluation of anticancer drug activity in human tumor cells in vitro," Anti-Cancer Drugs 9:531-538 (1998).

Ferguson et al. "Simultaneous monitoring of pH, $CO_2$, and $O_2$ using an optical imaging fiber" Analytica Chemica Acta, 1997, 340: 123-131.

Flora K and J Brennan, "Comparison of Formats for the Development of Fiber-Optic Biosensors Utilizing Sol-Gel Derived Materials Entrapping Fluorescently-Labeled Proteins." Analyst, 1999, 124, 1455-1462.

Ge X, et al., High Stability non-invasive autoclavable naked optical $CO_2$ sensor. 2003. Biosensor and Bioelectronics 18:pp. 857-865.

Gesinski et al., "Measurement of oxygen consumption of rat bone marrow cells by a polarographic method." J Appl Physiol. 1968; 24(6):751-754.

Guppy, J. Cell Phys. 170:1-7 (1997).

Handbook of Fluorescent Probes and Research Products published by Molecular Probes, Inc., Eugene, Oregon, USA, http://www.probes.com/handbook/ (accessed Mar. 12, 2004), Table of Contents, 2 pages.

Hasselbrink E.F. Jr., Shepodd T.J., Rehm J. (2002) "High-pressure microfluidic control in lab-on-a-chip devices using mobile polymer monoliths." Anal. Chem. 74, 4913-18.

Hua et al., "Microfluidic actuation using electrochemically generated bubbles." Anal. Chem. 74, 6392-96 (2002).

Huber et al., "Direct optical immunosensing (sensitivity and selectivity)," Sensors and Actuators B, 6, p. 122-126, 1992.

International Preliminary Report on Patentability for PCT/US2004/029163, Dec. 15, 2005, 15 pages.

International Preliminary Report on Patentability for PCT/US2007/013998, Jan. 22, 2009, 12 pages.

International Search Report and Written Opinion for PCT/US2004/029163, Mar. 2, 2005, 8 pages.

International Search Report and Written Opinion for PCT/US2007/013998, Apr. 8, 2008, 19 pages.

International Search Report for International Application No. PCT/US03/38294, Apr. 2004.

Invitation to Pay Additional Fees & Partial Internation Search for International Application No. PCT/US2007/013998, mailed Feb. 1, 2008.

Jin et al., "A biosensor concept based on imaging ellipsometry for visualization of biomolecular interactions," Analytical Biochemistry, 232, p. 69-72, 1995.

Jordan & Corn, "Surface Plasmon Resonance Imaging Measurements of Electrostatic Biopolymer Adsorption onto Chemically Modified Gold Surfaces," Anal. Chem., 69:1449-1456 (1997).

Lehmann et al., "Simultaneous measurement of cellular respiration and acidification with a single CMOS ISFET. 2001." Biosensors & Bioelectronics. 2001;16:195-203.

Ländesmäki I, Scampavia LD, Beeson C, and Ruzicka J. "Detection of Oxygen Consumption of Cultured Adherent Cells by Bead Injection Spectroscopy." Anal. Chem. 1999; 71: 5248-5252.

McConnell et al., "The Cytosensor Microphysiometer: Biological Applications of Silicon Technology" Science 257:1906 (1992).

Metzger et al., (2001) Toxicology 166, 97-108.

Morhard et al., "Immobilization of antibodies in micropatterns for cell detection by optical diffraction," Sensors and Actuators B, 70, p. 232-242, 2000.

Motterlini et. al., "Depression of Endothelial and Smooth Muscle Cell Oxygen Consumption by Endotoxin," American Journ. of Physio. vol. 275, No. 168 p. 776-782, Sep. 1998.

O'Riordan et al., "A cell viability assay based on monitoring respiration by optical oxygen sensor." Anal. Biochem. 2000; 278(2):221-227.

Office Action in Chinese Patent Application No. 200480029825, mailed Jul. 18, 2008.

Office Action in Chinese Patent Application No. 200480029825, mailed Nov. 28, 2008 (translation).

Office Action in Indian Patent Application No. 1170/DELNP/2006, mailed Oct. 6, 2008 (translation).

Official Action in European Patent Application No. 04788615.5-1234, dated Mar. 12, 2008, 4 pages.

Owicki et al., "The Light-Addressable Potentiometric Sensor: Principles and Biological Applications." Ann. Rev. Biophys. Biomol. Struct. 23: 87-113 (1994).

Paitan et al., "Monitoring Aromatics Hydrocarbons by Whole Cell Electrochemical Biosensors," Analytical Biochemistry, 335:175-183 (2004).

Panten et al., "$O_2$ consumption by isolated pancreatic islets, as measured in a Microincubation system with a Clark-type electrode." Endocrinology 1982; 111:1595-1600.

Parce et al., "Detection of Cell-Affecting Agents with a Silicon Biosensor." Science. 1989; 246(4927):243-247 (1989).

Pattison et al., "Measurement and Control of Dissolved Carbon Dioxide in Mammalian Cell Culture Processes Using an in Situ Fiber Optic Chemical Sensor." 2000 Biotechnology Prog. 16:769-774.

Pouli et al., (1998) "A phogrin-aequorin chimaera to image Ca2+ in the vicinity of secretory granules." Biochem. J., 330, 1399-1404.

Prokop et al., "NanoLiterBioReactor: long-term mammalian cell culture at nanofabricated scale," Biomedical Microdevices 6(4):325-339 (2004).

Robiolio et al., "Oxygen diffusion and mitochondrial respiration in neuroblastoma cells," Am. J. Physiol. 256 (6 Pt 1):C1207-1213 (Jun. 1989).

Rumsey et al., "Cellular Energetics and the Oxygen Dependence of Respiration in Cardiac Myocytes Isolated from Adult Rat" Journal of Biological Chemistry. 265(5):15392-15399 (1990).

Seaver et al. "Hydrogen Peroxide Fluxes and Compartmentalization inside Growing *Eschericha coli*"J. Bacteriol., 2001, 183: 7182-7189.

Shenoy MA, Biaglow JE, Varnes ME, Hetzel FW. "Inhibition of cultured human tumor cell oxygen utilization by chlorpromazine." Adv Exp Med Biol.1983;159:359-68.

Thorsen, T., Maerkl, S.J. and Quake, S.R. (2002) Microfluidic Large-Scale Integration Science 298, 580-586.

Tolosa L, Kostov Y, Harms P, Rao G. "Noninvasive measurement of dissolved oxygen in shake flasks." Biotechnol Bioeng Dec. 5, 2002;80(5):594-97.

Unger et al., (2000) Science 288, 113-116.

Vanderkooi et. al., "An Optical Method for Measurement of Dioxygen Concentration Based upon Quenching of Phosphorescence," J. Biol. Chem., 262 (12):5476-5482 (Apr. 1987).

Wada et al., (1993) "GM-CSF Triggers a Rapid Glucose Dependent Extracellular Mediated Activation of Acid Production." J. Cell Physiol. 154: 129-138.

Wiley, C and Beeson, C. (2002) "Continuous measurement of glucose utilization in heart myoblasts." Analytical Biochemistry 304, 139-146.

Wilson et al., "The Oxygen Dependence of Mitochondrial Oxidative Phosphorylation Measured by a New Optical Method for Measuring Oxygen Concentration," J. Biol. Chem., 263:2712-2718 (1988).

Wodnicka et al. "Novel fluorescent technology platform for high throughput cytotoxicity and proliferation assays." Journal of Biomolecular Screening. 2000; 5:141-152.

Wolfbeis OS, 2002. "Fiber-Optic Chemical Sensors and Biosensors." Annal of Chem. 2002; 74:2663-2678.

METHOD AND DEVICE FOR MEASURING EXTRACELLULAR ACIDIFICATION AND OXYGEN CONSUMPTION RATE WITH HIGHER PRECISION

CROSS-REFERENCE TO RELATED APPLICATION

This application claims priority to and the benefit of U.S. Provisional Patent Application No. 61/105,201, filed Oct. 14, 2008, which is hereby incorporated herein by reference in its entirety.

FIELD OF THE INVENTION

The present invention relates generally to high throughput screening techniques and, more specifically, to measurements of the acidification rate and oxygen consumption rate of an extracellular medium surrounding cells.

BACKGROUND

Living cells convert nutrients to energy and various chemical byproducts through a series of oxidation and reduction reactions. By monitoring the byproducts excreted into, or taken up from, the extracellular medium, one can gain information about the underlying metabolic pathways and associated metabolic rates. This knowledge, in turn, can be useful in determining cell viability, studying the mechanisms underlying various diseases, and screening new drug candidates for effectiveness as well as unexpected or adverse effects. For example, the combined measurement of at least two of oxygen consumption rate (OCR), extracellular acidification rate (ECAR), and $CO_2$ production rate (CPR) can discriminate between glucose and fatty acid oxidation, and thereby serve as a basis for testing drugs targeting obesity or diabetes. Similarly, extracellular flux rate measurements can be used in developing cancer therapies which exploit differences in the relative utilization of aerobic and anaerobic metabolic pathways between cancerous and non-cancerous cells.

Extracellular flux rates can be quantified with a variety of sensors, including, e.g., fluorescent sensors, ISFET sensors, and amperometric sensors such as the Clark electrode. For reliable detection, device sensitivity herein sets a lower bound for the analyte concentration, which translates into a minimal required cell density. Typically, cell densities sufficiently high for measurements are too high for maintaining cell viability and growth. This conflict can be resolved with apparatus that allow for low cell densities for cell maintenance, and temporarily increased densities during measurement. One such apparatus has been described in U.S. Pat. No. 7,276,351 (Teich et al., "Method and device for measuring multiple physiological properties of cells"), the disclosure of which is incorporated herein by reference. It utilizes a vessel holding cells in a medium, such as a microtiter well plate, and a plunger which can be immersed into a well to create a reduced volume for measurements.

Separating the byproducts of metabolic reactions from molecules of the same type, but different origin, that are present in the environment is another challenge encountered in measuring extracellular fluxes. Usually, analyte background flux is measured in blank (i.e., cell-free) sample, and subtracted from the fluxes measured in medium in the presence of cell cultures. For example, when using a well plate for cell-based assays, one of the wells may serve as the reference well. This approach produced satisfactory results, provided that the background rate is uniform across the plate and low compared with the total flux.

SUMMARY OF THE INVENTION

The present invention is based on the observation that in measurements of $CO_2$ flux or acidification rate, the background rates often show large fluctuations in time and between different wells, which significantly impede the experiments, and on the discovery that high background fluxes in $CO_2$ and ECAR measurements are a consequence of $CO_2$ outgassing from the cell-containing vessel. Cell cultures typically are incubated in a $CO_2$ rich atmosphere, resulting in $CO_2$ uptake by the vessel, which may, for instance, be formed from a molded polymer such as polystyrene. Assays are later performed under standard atmospheric conditions, which permits $CO_2$ outgassing from the vessel into the cell-containing medium. The $CO_2$ then reacts with water to form carbonic acid, thereby acidifying the medium. This effect is greater as the surface-to-volume ratio of the medium-holding vessel increases. Whereas in measurements in well plates of conventional media volume, the ratio is sufficiently low to permit reasonably accurate and precise background-corrected ECAR measurements, as the ratio increases, it increasingly causes well-to-well variations and imprecision. Moreover, outgassing becomes an increasing concern as high-throughput equipment is scaled to higher numbers of compartments with correspondingly decreased compartment size in an effort to accommodate increasing numbers of simultaneous cell-based assays.

The present invention provides systems and methods for measuring, with improved accuracy and precision, the extracellular acidification rate or $CO_2$ evolution of cell cultures held in compartments of small volume. Embodiments of the invention also are characterized by permitting inherently more precise oxygen consumption rate measurements, as low gas permeability materials used to reduce $CO_2$ outgassing also reduce oxygen flux across the walls of the media compartment(s) and promote isolation of changes in oxygen concentration caused by cell metabolism. Apparatus for such cell-based assays include well-plates (e.g., 24- or 96-well plates) and microfluidic devices The invention is based on the discovery that through the use of materials having low gas permeability, i.e., low permeability for $CO_2$ and oxygen, uptake during incubation of the cell cultures and subsequent $CO_2$ outgassing can be abated to a level that impedes measurements less and permits improved ECAR precision and accuracy. Such materials include, in particular, polyethylene terephthalate (PET), which is a moldable polymer suitable for use in well plates and other vessels for cell-based assays.

Accordingly, the present invention provides, in a first aspect, an apparatus for measuring extracellular acidification rate, $CO_2$ evolution, and/or oxygen consumption rate of a cell culture in a medium. The apparatus contains one or more compartments, typically an array of compartments, for holding cells disposed within a cell medium. The ratio of the area of an interior surface, defined as the contact area of the medium with the compartment walls that are exposed to high $CO_2$ concentrations during incubation, to the volume of the medium during the measurement, is greater than 2.0 $mm^2/mm^3$, and at least a portion of the interior surface has a carbon dioxide permeability coefficient, that is a carbon dioxide and oxygen permeability coefficient, less than $8\times10^{-9}$ grams per meter-second. Herein, the permeability coefficient is defined as the product of the diffusion coefficient of the gas in the material, and the solubility measured in mass of gas per volume of the material. In some embodiments, the one or more compartments are serviced by a microfluidic conduit, which transports media to or from the cells.

In another aspect, the invention provides an apparatus for measuring extracellular acidification rate, $CO_2$ evolution, or oxygen consumption rate of a cell culture in a medium which includes a compartment defined by a well, and a moveable barrier which alters the volume of the medium in the well about the cells between a larger and a smaller volume. When the barrier is in the position defining the smaller volume, the well defines an interior surface in contact with the medium whose area divided by the volume of the medium is greater than $2.0\ mm^2/mm^3$. The interior surface has a carbon dioxide permeability coefficient less than $8\times10^{-9}$ grams per meter-second.

In various embodiments of these two aspects, the compartment is formed (at least in part) by a molded polymer characterized by having said low oxygen/carbon dioxide permeability coefficient or an oxygen/carbon dioxide diffusion coefficient less than $5\times10^{-12}\ m^2/s$. In other embodiments, the compartment includes a coating characterized by the low gas permeability or diffusion coefficient. In particular, the $CO_2$ permeability coefficient may be low enough to reduce $CO_2$ transport from the surface of the compartment into the medium, or oxygen transport across the compartment wall, to a level that allows one to infer the metabolic activity of the cells in culture from measurements of oxygen consumption rate (OCR), cell-induced ECAR or $CO_2$ evolution, as a result of sufficiently improved accuracy or precision of measurement. A material that meets the requirement of low gas permeability is polyethylene terephthalate.

Some embodiments of the apparatus contain a plurality of wells defining the compartments. In particular, in one embodiment, the apparatus includes an array of 96, or even 384 wells. The wells may define stops which limit the movement of a barrier used to define a smaller volume during measurements. In various embodiments, the apparatus further includes a sensor for measuring acidification rate or $CO_2$ evolution in the extracellular medium. The sensor may be disposed within the compartment.

In yet another aspect, the invention provides a method for measuring a property of the physiological state of cells cultured in a $CO_2$-rich environment by measuring the cell-induced acidification of the extracellular medium. The method involves providing a compartment for holding cells disposed within a cell medium whose interior surface has a $CO_2$ permeability coefficient less than $8\times10^{-9}$ g/(m·s); adding cells and a volume of medium to the compartment, and setting the ratio of the contact area of the interior surface with the medium to the volume of the medium to a value greater than $2.0\ mm^2/mm^3$; and measuring $H^+$ or $CO_2$ concentration change in the volume over a time interval. By providing a container of low $CO_2$ permeability, the migration of $CO_2$ from the compartment structure into the medium is reduced during or before the measurement, and accuracy or precision of the measurement is thereby improved. Also, such materials also have low oxygen permeabilities and precision of OCR also is improved. The specified surface-to-volume ratio can be achieved by adding an adequate amount of medium, by moving a barrier that alters the volume of medium about the cells from a larger to a smaller volume. In alternative embodiments, it may be achieved by closing one or more valves in the inlet and/or outlet channels feeding media to the compartment, thereby stopping or temporarily inhibiting flow through the compartment, setting the volume of extracellular medium available to the cells for mass transfer to a small fixed value, and enabling a more precise measurement.

In various embodiments, a molded plate with multiple wells, e.g., a 24-well or 96-well plate, is provided. Further, apparatus comprising one or more compartments serviced by a microfluidic conduit may be provided. In some embodiments, the method involves measuring hydrogen ion or carbon dioxide concentration change using a sensor disposed in contact with the medium. The sensor may utilize a fluorophore with an optical property that changes as a function of ion concentration.

DETAILED DESCRIPTION OF THE INVENTION

In a typical multiplexed cell-based assay of the type described in U.S. Pat. No. 7,276,351, at the outset the cells are seeded into wells of a multi-well plate containing a tissue-culture, and subsequently allowed to equilibrate and grow in an incubator at 37° C. and under an atmosphere containing 5%-10% $CO_2$, to a population density suitable for the experiment. The incubation period, beginning at the time of seeding, is typically greater than 24 hours. During this time, $CO_2$ is absorbed by the medium in the wells and the well plate itself, which is often fabricated from a molded polymer such as polystyrene or polycarbonate blend materials. This $CO_2$ absorption continues until the well plates are removed from the incubator or until the materials reach equilibrium with the carbon-dioxide-rich environment. Following incubation, the well plates are placed into a measuring apparatus, which is typically outside the incubator. Measurements of extracellular solute flux take place at standard atmosphere, whose carbon dioxide concentration is about 0.4%—significantly lower than in the incubator. This change in atmospheric $CO_2$ concentration creates a partial pressure or concentration gradient, causing $CO_2$ gas to migrate from the well plate into the environment, until equilibration is achieved at the lower pressure.

Figure 1:
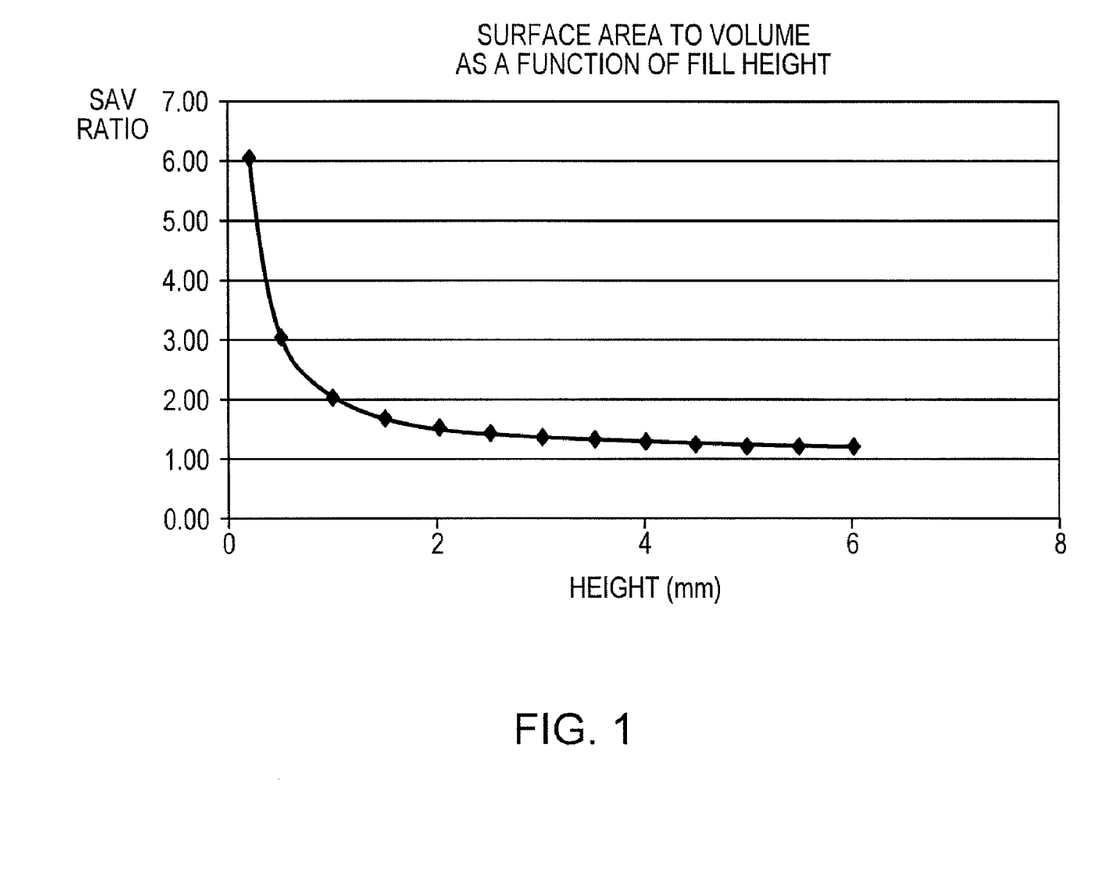
FIG. 1 is a graph illustrating the surface-area-to-volume ratio of a microtiter plate well as a function of fill height.

If, as is often desired, the measurement is to be made within hours or perhaps a day after removal of the plate from the incubator, carbon dioxide flux from the vessel material into the extracellular medium constitutes a background flux during ECAR measurements. Its contribution relative to the fluxes of interest, i.e., metabolic $CO_2$ production rate (CPR) and/or proton production rate (PPR), and the resulting rate of change of the pH (ECAR), depends, among other factors, on the ratio of the contact area between the vessel and the medium, and the volume of medium. Herein, the crucial volume of medium is the measurement volume, as opposed to the fill volume. In some embodiments of the invention, the effective extracellular volume is temporarily decreased during measurements to achieve higher signals, e.g., the volume of medium about the cells is temporarily reduced by movement of a barrier so that the small amount of $CO_2$ emitted from the cells is concentrated in the small test volume and not dissipated through a larger maintenance volume. A typical well plate has well diameters on the order of a few millimeters, and the medium volumes per well on the order of one milliliter. For example, Seahorse Biosciences is producing a 24-well plate (XF24) with a 6 mm well diameter, and a 96-well plate (XF96) with a 3.8 mm well diameter. FIG. 1 illustrates the surface area to volume ratio of medium in the well of an XF96 microtiter plate as a function of the height of the cylindrical column of medium. Since the volume is proportional to the height, whereas the total surface area includes a constant contribution (the area of the bottom surface) in addition to the sidewall area (which is proportional to the height), the surface-area-to-volume (SAV) ratio increases with decreasing height of the column of medium. Below about 2 mm high, the increase in surface area becomes significant. Between a typical fill height of 6 mm and a typical measurement height of 0.2 mm, the SAV ratio grows almost five-fold.

In addition to the contact area between well plate and medium, the rate of outgassing depends on the difference between $CO_2$ concentrations or partial pressures in the well plate material and the medium, and the $CO_2$ permeability of the well plate material. The permeability coefficient, in turn, is related to the diffusion coefficient of the material and its $CO_2$ solubility, i.e., the amount of $CO_2$ it absorbs per unit volume at standard pressure. Specifically, if carbon dioxide extrusion rate is denoted by R, contact surface area by A, partial $CO_2$ pressure by p, standard atmospheric pressure by $p_0$, $CO_2$ concentration by c, the dimension perpendicular to the contact surface by x, the diffusion coefficient by D, the solubility coefficient at standard pressure by S, and the permeability coefficient by P, then the extrusion rate can be calculated according to:

$$R = A \cdot D \cdot \frac{dc}{dx} = A \cdot D \cdot S \cdot \frac{d(p/p_0)}{dx} = A \cdot P \cdot \frac{d(p/p_0)}{dx}$$

TABLE 1 lists diffusion, solubility, and permeability coefficients for various materials suitable, in principle, for use in cell culture vessels such as well plates. (The solubility measured in grams of gas dissolved per volume of the specified material is related to the solubility measured in volume of gas per volume of material through the molar volume of gas and the molar weight of carbon dioxide.)

TABLE 1

Diffusion and permeation properties of various moldable polymers

| Material | Diffusion coefficient $(m^2/s)$ | Solubility coefficient $(m^3 STP/m^3)$ | Solubility coefficient $(kg/m^3)$ | Permeability coefficient $(g/m \, s)$ |
|---|---|---|---|---|
| Polystyrene (PS) | $5.8 \cdot 10^{-12}$ | 0.8 | 1.5 | $8.9 \cdot 10^{-9}$ |
| Polypropylene (PP) | $1.4 \cdot 10^{-11}$ | 0.17 | 0.3 | $4.7 \cdot 10^{-9}$ |
| Polyvinyl Chloride (PVC) | $2.5 \cdot 10^{-13}$ | 0.47 | 0.9 | $2.4 \cdot 10^{-10}$ |
| Polyethylene Terephthalate (PET) | $5.4 \cdot 10^{-14}$ | 1.4 | 2.7 | $2 \cdot 10^{-10}$ |

From among these materials, the permeability coefficient of PET is the lowest, due to its low diffusion coefficient. Polyethylene terephthalate is therefore a preferred material for the manufacture of cell chambers used in embodiments of the methods and apparatus of the present invention, which aim at reduced carbon dioxide outgassing by replacing high-permeability substances, such as polystyrene, a commonly used well-plate material. However, materials with low $CO_2$ permeability also may be used. Diffusion coefficient is a key property of the material, or a coating on the material in contact with the medium. Typically, the coefficient will be different in a given material for different gases, but a material with a low $CO_2$ diffusion coefficient typically also will have a lower oxygen diffusion coefficient, and a lower ammonia diffusion coefficient, and this is advantageous in improving precision of measurement of these gases in the extracellular media.

Well plates (XF24) made from PET and polystyrene ("control") were compared and tested with PPR and ECAR measurements in a Seahorse Biosciences XF24 instrument. The results are illustrated in FIGS. 2A, 2B, 2D, 2E, 3A and 3B.

Figure 2A:
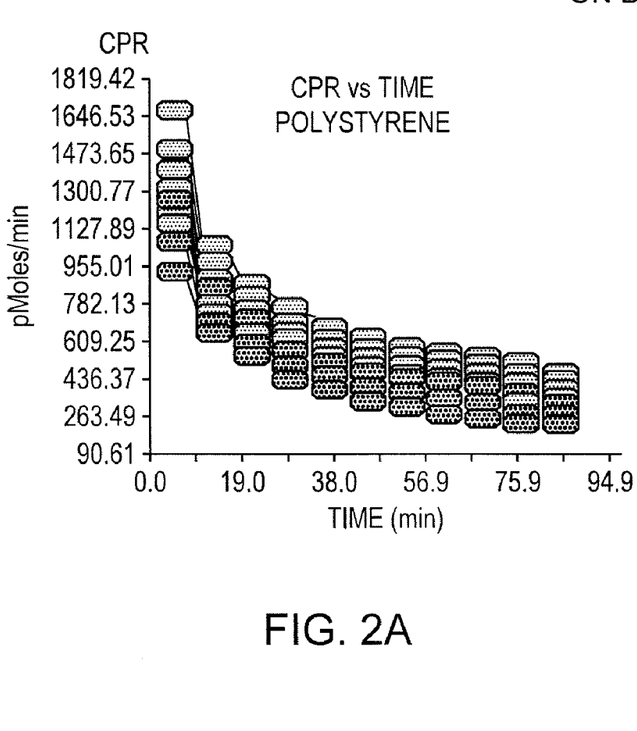
FIG. 2A is a graph illustrating the background $CO_2$ production rate in a media-containing polystyrene well plate.
Figure 2B:
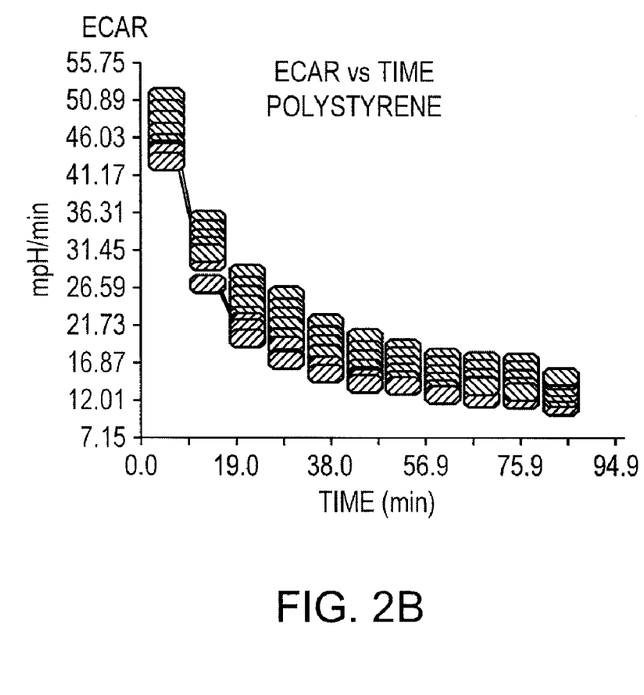
FIG. 2B is a graph illustrating the background extracellular acidification rate in a media-containing polystyrene well plate.
Figure 2C:
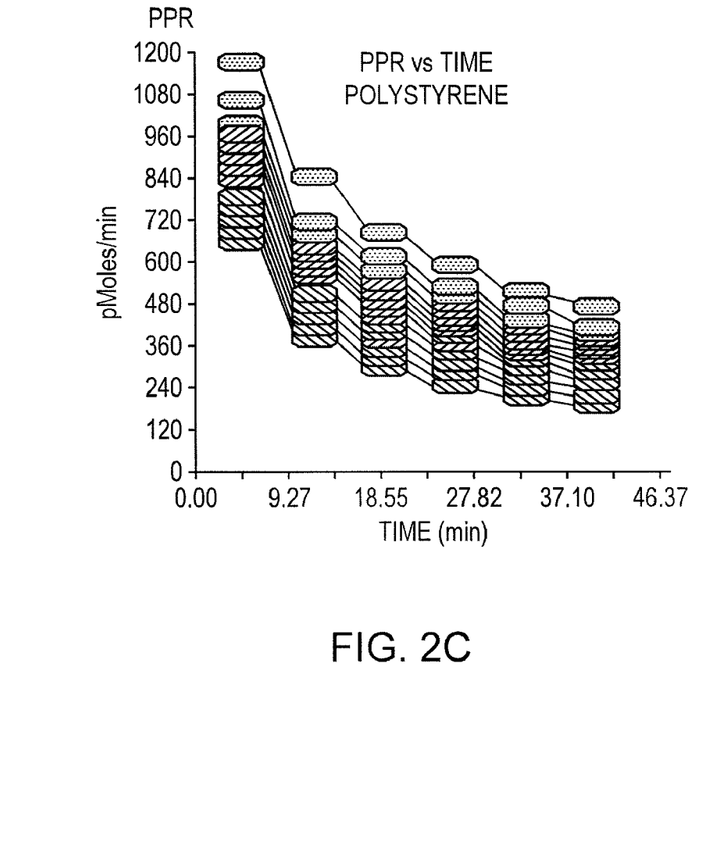
FIG. 2C is a graph illustrating the background proton production rate for well plates made from polystyrene.

Experiment 1: To determine background analyte flux rates in conventional well plates, phosphate-buffered cell culture media (Dulbecco's Modified Eagle's Medium, DMEM) was placed into the wells of XF 24 cell culture plates made from polystyrene. The plates were equilibrated overnight in an incubator at 37° C. and under a 10% $CO_2$ atmosphere. After the equilibration period, the plates were removed from the incubator, and media within the wells was replaced with fresh unbuffered DMEM. Carbon dioxide production rate, pH change rate, and oxygen consumption rate were measured over a period of 85 minutes using an XF24/3 sensor head. The measurement volume was approximately 7 μl, and the SAV ratio approximately 6. FIGS. 2A-2B show the results of this test. The different grey scale data point values in each vertical column correspond to different wells. Note that while $CO_2$ flux (CPR) and extracellular acidification rate (ECAR—here just pH change as no cells are present) declined significantly over the test period, the oxygen consumption rate (OCR) stayed approximately constant. The $CO_2$ flux and acidification rate decreased by a factor of about 4 between the beginning and end of the test period, indicating that $CO_2$ outgassing significantly affects rate measurements in standard polystyrene plates.

Experiment 2: Aliquots of phosphate-buffered cell culture media were placed into wells of 24-well plates molded from polystyrene and from PET. The plates were equilibrated overnight in an incubator at 37° C. and under a 10% $CO_2$ atmosphere, and then removed from the incubator. Media within the wells then was replaced with fresh unbuffered DMEM. Proton production rate was measured over a 45 minute period.

Figure 2D:
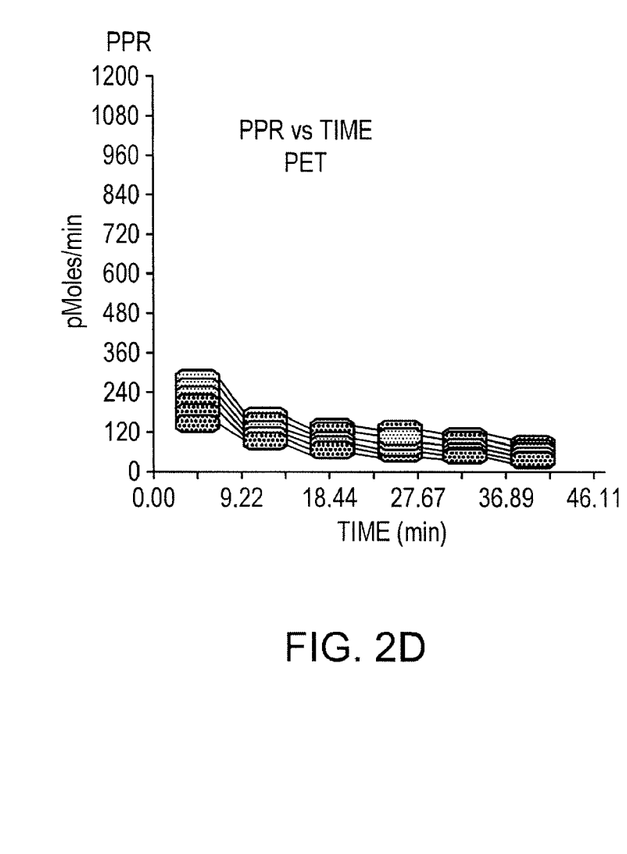
FIG. 2D is a graph illustrating the background proton production rate for well plates made from polyethylene terephthalate.

FIGS. 2D and 2E show the PPR (in picomoles per minute) as a function of time for both the polystyrene plate (left) and the PET plate (right). Again, the different grey scale values correspond to different wells. As the data indicate, the background rate for PET is about fourfold lower than that for polystyrene, and its variation across the wells is significantly reduced.

Figure 3A:
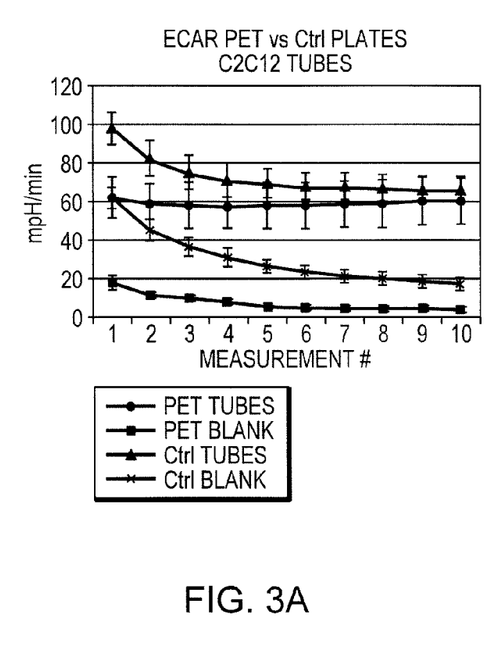
FIG. 3A is a graph illustrating the extracellular acidification rate caused by cell cultures in medium for well plates made from polystyrene (control tubes) and polyethylene terephthalate.
Figure 3B:
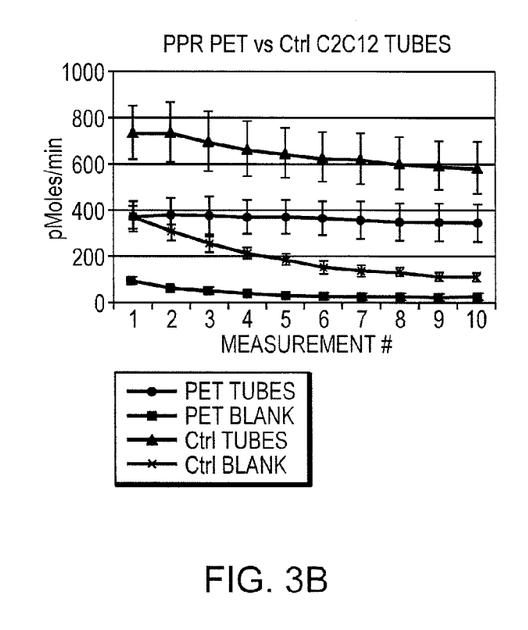
FIG. 3B is a graph illustrating the proton production rate caused by cell cultures in medium for well plates made from polystyrene (control tubes) and polyethylene terephthalate.

Experiment 3: C2C12 cells were placed into 24-well culture plates of polystyrene and PET, and differentiated over seven days into multicellular tubes. During the differentiation period, the cells remained in phosphate-buffered media in a 10% $CO_2$ incubator. Following incubation, the plates were removed from the incubator, and the media was replaced with fresh unbuffered DMEM. Metabolic activity of the cell tubes was subsequently measured in the XF24 instrument, using a 24/3 sensor head to measure ECAR and PPR. The measurement volume was approximately 7 μl, and the SAV ratio approximately 6. The data are illustrated in FIGS. 3A and 3B, respectively. Along with the rates measured for Experiment 3, the rates for blank (polystyrene) samples from Experiment 2 are shown. Note the empty tubes ("control blanks") and cell-containing tubes ("control tubes") of polystyrene exhibit a decline in pH over time (ECAR and proton production rate data), whereas the polyethylene terephthalate blanks exhibit substantially constant pH and PET tubes containing cells show a much smaller pH decline. These experimental results demonstrate the utility of PET plates in ECAR and related measurements.

Figure 4A:
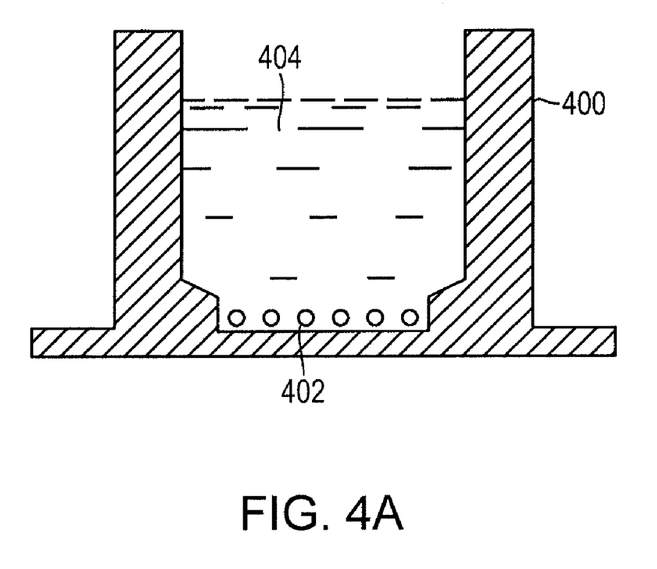
FIG. 4A is a schematic cross sectional view of a well according to an embodiment of the invention.
Figure 4B:
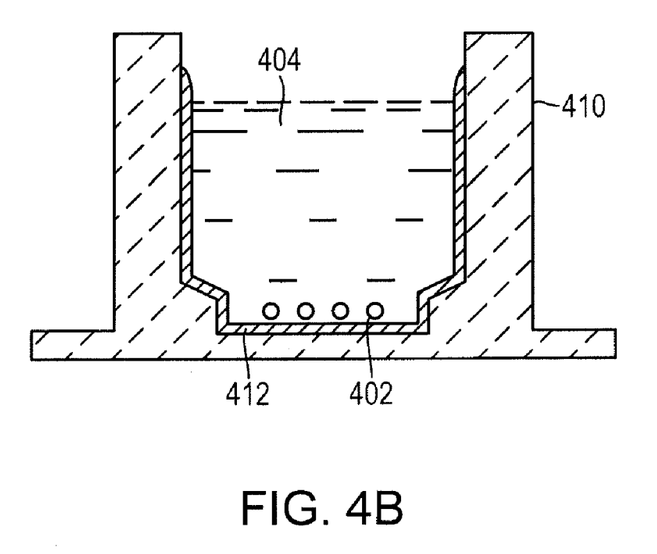
FIG. 4B is a schematic cross sectional view of a well according to another embodiment of the invention.

Materials exhibiting low $CO_2$ permeability (either by way of low solubility of low diffusivity constant, or both), as described above, can be employed to advantage in a variety of devices for measuring ECAR or $CO_2$ evolution as well as oxygen consumption, including well plates and microfluidic devices. Polyethylene terephthalate is a suitable substitute for more commonly used high-permeability materials not only because of its particularly low permeability coefficient, but also because it can be molded into the desired shape with the same equipment as other thermoplastics. FIG. 4A illustrates, in a schematic cross-sectional side view, a representative embodiment of a well defined by a structure 400 fabricated of PET or another low-permeability moldable polymer. Cells 402 can be placed on the bottom of the cylindrical well. Alternatively or additionally, cells may adhere to the vessel walls. The well is filled with medium 404 containing a sufficient amount of nutrients to sustain the cells for a reasonable time. Typical embodiments contain a plurality of such wells, e.g., an array of 96 wells or more, as currently used for standard high-throughput assays. FIG. 4B illustrates an alternative embodiment, in which the bulk material 410 of the well plate is arbitrary, but the wells are coated with a material 412 with low $CO_2$ permeability coefficient, at least in some portions of the surface area. The coating material may be PET, but other coatings having low $CO_2$ permeability may be used, e.g., materials with a permeability coefficient of less than $8 \times 10^{-9}$ grams per meter-second, preferably less than $5 \times 10^{-9}$ grams per meter-second, more preferably less than $3 \times 10^{-9}$ grams per meter-second, and most preferably less than $3 \times 10^{-10}$ grams per meter-second. For example, hydrogenated amorphous carbon films can be plasma-deposited onto the well. Such coatings have been proven as carbon dioxide barriers in bottles containing carbonated soft drinks or beer.

Figure 4C:
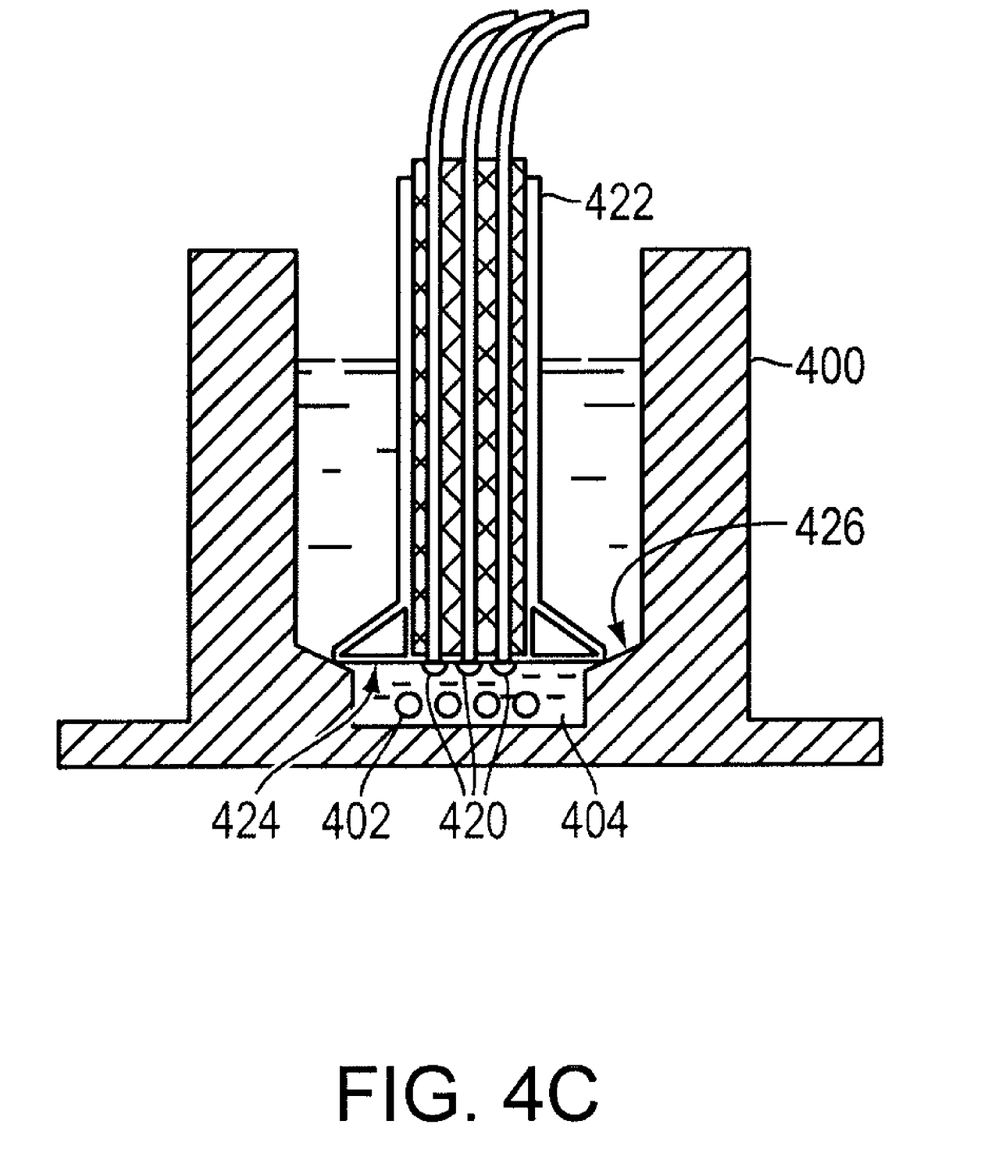
FIG. 4C is a schematic cross sectional view of a well according to yet another embodiment of the invention.

Protons and carbon dioxide or oxygen concentration, and changes in the concentration over time, in the extracellular medium can be detected with a variety of sensors, including ion-sensitive field effect transistors (ISFET), fluorescent sensors, potentiometric sensors, optical or microwave sensors, or sensors based on surface plasmon resonance, optical diffraction, or Woods anomaly. FIG. 4C shows the well of FIG. 4A during measurement. Herein, a sensor 420 (in the illustration, a triplet of sensors) is configured at one end of a plunger 422, which can be immersed into the medium-holding well. As illustrated, the plunger can form a barrier 424 that effectively reduces the volume of the medium 404 about the cells. The cell density, i.e., the number of cells divided by the volume of medium available for mass transfer, accordingly is temporarily increased. As a result, the analyte concentrations change faster than they would in a larger volume, and, therefore, the measured signal and signal to noise ratio is higher. The well may be shaped such as to provide a mechanical stop 426 for the movement of the barrier 424. Further detail on the use of a plunger is provided in U.S. Pat. No. 7,276,351, incorporated by reference herein. In embodiments using a coating instead of a bulk material with low $CO_2$ permeability, the portion of the well surface surrounding at least the measuring volume is preferably (but not necessarily) completely coated. The plunger material is generally not of concern, as the plunger, though interfacing with the measurement volume during measurements, normally is not in contact with a $CO_2$-rich atmosphere during typical experiments.

Figure 5A:
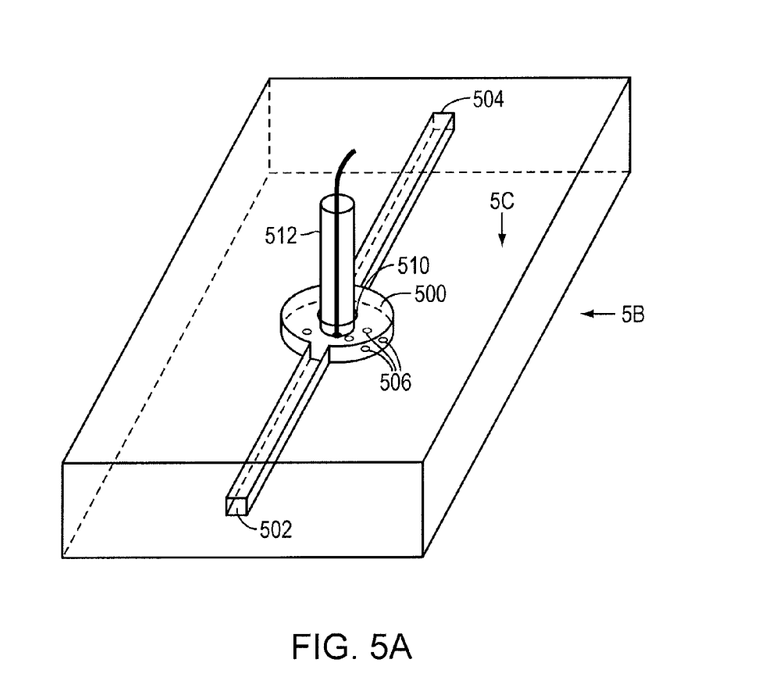
FIG. 5A is a schematic perspective view of a microfluidic device according to one embodiment of the invention.
Figure 5B:
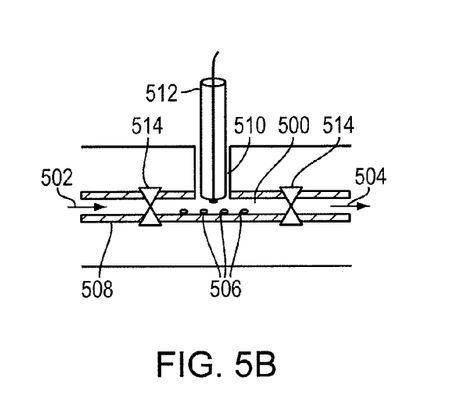
FIG. 5B is a side view of a microfluidic device according to one embodiment of the invention.
Figure 5C:
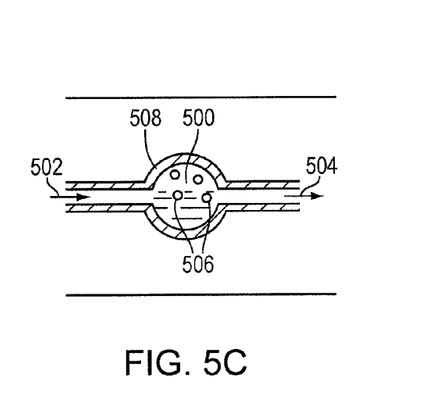
FIG. 5C is a top view of a microfluidic device according to one embodiment of the invention.

An exemplary microfluidic device which can embody the invention is schematically illustrated in FIGS. 5A-C. As illustrated, an enclosed compartment 500, serviced by an inlet channel 502 and an outlet channel 504, holds the cells 506 and cell media. During incubation, the device is filled with media having a high $CO_2$ content. When the cell culture has reached the desired cell density, media can be exchanged by perfusing the device with fresh, low-$CO_2$ buffer. To prevent or diminish $CO_2$ uptake during incubation, the interior surface of the device, or portions thereof, can be coated with a layer 508 of a material having low permeability for $CO_2$, as illustrated in the side view of FIG. 5B and the top view of FIG. 5C. Alternatively, the device can be fabricated from such a low-$CO_2$-permeability material in whole. To enable ECAR measurements, the compartment 500 may have an opening 510, through which a sensor 512 can be immersed into the extracellular medium. During measurements, valves 514 to one, preferably both sides of the cell-containing compartment 500 (symbolically illustrated in FIG. 5B) close the inlet and outlet channels 502, 504 to ensure a small measurement volume. In between measurements, the valves are open to allow for a flux of medium through the chamber, as will be necessary to provide the cells with sufficient nutrients, and to dissipate metabolic byproducts, which, in too high concentrations, would affect cell viability.

The embodiments described in FIGS. 4A-4C and 5A-5C serve illustrative purposes. As will be apparent to those of skill in the art, various modifications and combinations of the features described are possible, and within the scope of the invention. For example, microfluidic service channels may be incorporated into well plates.

Apparatus according to the invention can be manufactured with techniques well known in the art. Well plates may, for example, be fabricated by injection molding. Microfluidic devices may be produced, for example, by means of lithography. A common method includes patterning a substrate, e.g., a silicon wafer spin-coated with photoresists, by photolithography, etching the pattern into the substrate to form an inverse cast for molding, replica-molding a polymer layer having the desired microchannels and compartments. Generally, various fabrication techniques are available to the skilled artisan.

Figure 6:
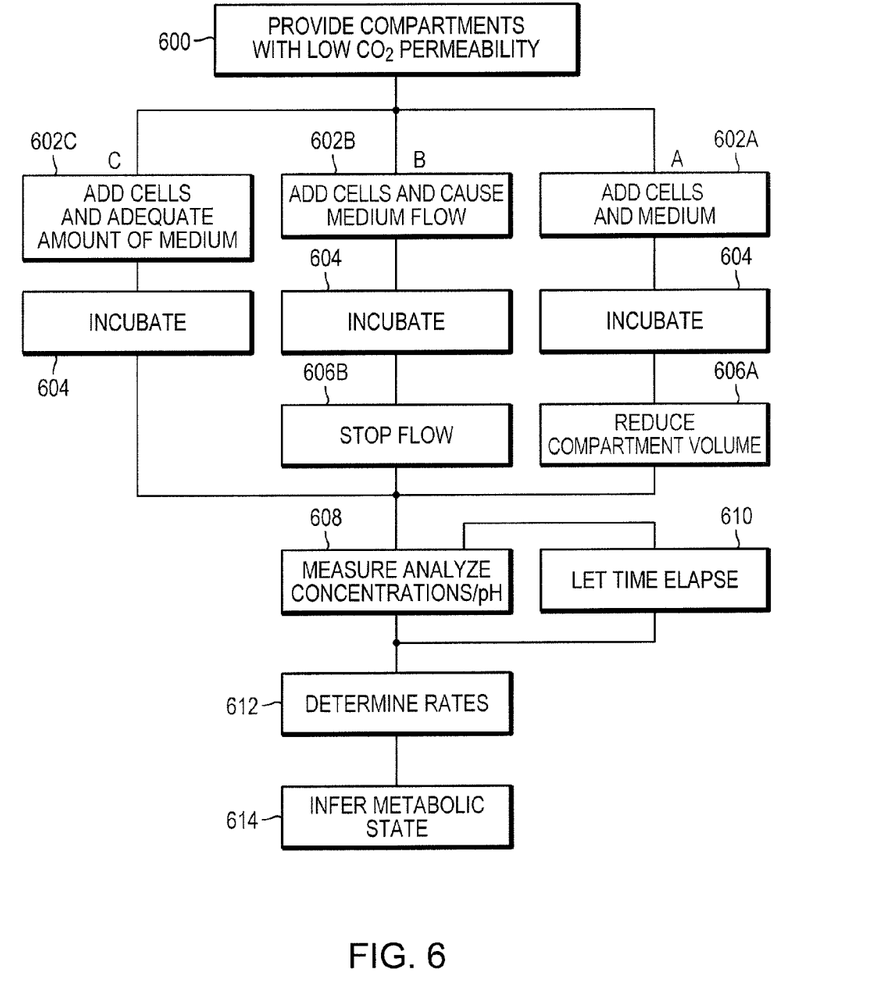
FIG. 6 is a flow chart illustrating a method of measuring the metabolic state of cells according to some embodiments of the invention.

FIG. 6 is a flow chart illustrating a method of using devices as described above to obtain data of increased precision and accuracy. In a first step 600, a device with one or more compartments characterized by low $CO_2$ permeability is provided. In subsequent steps, when the compartments are filled with medium, one of several paths is followed to ensure that the volume of medium in respective compartments is sufficiently low during measurements to permit high resolution determination of proton and/or $CO_2$ concentration. The choice of the path depends on the type of device used. On path A, cells and medium are added to the device (step 602A), the cells are incubated (step 604), and, during measurements, the volume of medium in communication with the cells is reduced, e.g., with a barrier (step 606A). On path B, a low volume compartment is seeded with cells, and a continuous flow of medium through the compartment serves to maintain the cells and permit their expansion during incubation and in between measurements. During measurements, the medium flow is stopped, e.g., by valves, and solute concentration changes are measured in the small, now isolated volume. On path C, a small, temporarily adequate amount of medium is added to a compartment containing cells, e.g., cells previously cultured in a $CO_2$ atmosphere to a desired density. The amount of medium added is sufficiently small so as to permit measurement of extracellular solute flux. The three illustrated paths are exemplary only, and may be combined or modified in further embodiments of the invention. In all cases, because of the property of the interface between the medium and the material of the compartment, $CO_2$ outgas sing into the medium during the course of the measurement interval is significantly reduced.

Thus, in step 608, one or more analyte concentrations are measured. For example, a sensor head may measure proton concentration, or carbon dioxide concentration, and optionally gather concentration data from other solutes, e.g., oxygen or lactate. To determine the rate of change, the measurements are repeated; subsequent measurements are separated by a predetermined, typically short time period (step 210). The time-dependent data then may be used to calculate analyte production rates and/or acidification rate (step 212). Finally, the measured rates may be used to gain insight into the metabolic state of the cells (step 214). For example, in aerobic respiration, the quotient between CPR and OCR indicates which substrate is being consumed. For glucose respiration, the quotient is ~1; for protein it is ~0.82; for fat it is ~0.7; and for ethanol it is ~0.67. In anaerobic respiration, lactate contributes significantly to the acidification of the medium. The amount of lactate produced can be inferred from the ratio of pH and $CO_2$ concentration.

What is claimed is:

1. An apparatus for measuring extracellular acidification rate or $CO_2$ evolution of a cell culture disposed in a medium, the apparatus comprising:
   a compartment defining an interior surface and a volume for holding cells disposed within a cell medium;
   a ratio of an area of said interior surface to a volume of the cell medium being greater than 2.0 $mm^2/mm^3$;
   at least a portion of said interior surface designed for contact with said volume of the cell medium having a carbon dioxide permeability coefficient less than $8 \times 10^{-9}$ grams per meter-second.

2. An apparatus for measuring extracellular acidification rate or $CO_2$ evolution of a cell culture disposed in a medium, the apparatus comprising:
   a compartment defined by a well defining a volume for holding cells and a medium;
   a moveable barrier which alters a volume of the medium in the well about the cells between a larger and a smaller volume, the well, when said barrier is in position defining said smaller volume, defining an interior surface in contact with the medium;
   a ratio of an area of said interior surface to a volume of the medium when said barrier is in position defining said smaller volume being greater than 2.0 $mm^2/mm^3$;
   the interior surface of at least said well having a carbon dioxide permeability coefficient less than $8 \times 10^{-9}$ grams per meter-second.

3. The apparatus of claim 1 or 2 wherein the compartment comprises a coating characterized by having said low carbon dioxide permeability coefficient.

4. The apparatus of claim 1 or 2 wherein the compartment comprises a molded polymer characterized by having said low carbon dioxide permeability coefficient.

5. The apparatus of claim 1 or 2 comprising a plurality of wells comprising plural said compartments.

6. The apparatus of claim 5 comprising an array of 96 said wells.

7. The apparatus of claim 5 wherein said wells define stops for limiting the movement of a barrier to define a smaller volume therein.

8. The apparatus of claim 1 wherein the compartment is serviced by a microfluidic channel for transporting media to or from the cells.

9. The apparatus of claim 1 or 2 further comprising a sensor for measuring acidification rate, oxygen consumption rate, or $CO_2$ evolution in extracellular medium.

10. The apparatus of claim 9 wherein said sensor is disposed within said compartment.

11. The apparatus of claim 1 or 2 wherein said compartment comprises a molded polymer characterized by a low carbon dioxide diffusion coefficient less than $5 \times 10^{-12}$ $m^2$/second.

12. The apparatus of claim 1 or 2 wherein said interior surface comprises polyethylene terephthalate.

13. The apparatus of claim 1 or 2 wherein said carbon dioxide permeability coefficient is sufficiently low to reduce carbon dioxide transport from the interior surface of the compartment into the medium to permit improved accuracy or precision of measurement of cell-induced extracellular acidification rate or $CO_2$ evolution sufficient to infer the metabolic activity of cells in the cell culture.

14. A method for measuring a property of a physiological state of cells cultured in a $CO_2$-rich environment by measuring cell-induced solute changes in an extracellular medium, the method comprising the steps of:
   A) providing a compartment defining an interior surface having a gas permeability coefficient less than $8 \times 10^{-9}$ grams per meter-second and a volume for holding cells disposed within a medium;
   B) adding cells and a volume of medium to said compartment and setting a ratio of the area of the interior surface of said compartment in contact with said medium to the volume of said medium greater than 2.0 $cm^2/cm^3$; and
   C) measuring hydrogen ion, oxygen, or carbon dioxide concentration change over a time interval;
   thereby to reduce migration of carbon dioxide or oxygen from the compartment structure into the medium during or before the measurement and to improve accuracy or precision of the measurement.

15. The method of claim 14 comprising providing a molded plate defining multiple wells defining multiple said compartments.

16. The method of claim 14 comprising providing a 96-well molded plate.

17. The method of claim 14 comprising providing a said compartment serviced by a microfluidic conduit for media transport to or from said compartment.

18. The method of claim 14 wherein step B comprises adding sufficient medium to said compartment to produce said ratio.

19. The method of claim 14 wherein step B comprises moving a barrier to alter the volume of the medium in the compartment about the cells from a larger to a smaller volume, the well, when said barrier is in position defining said smaller volume, defining said interior surface in contact with the medium.

20. The method of claim 14 wherein step B comprises closing a valve in a microfluidic conduit servicing the compartment to temporarily inhibit flow of medium through the compartment.

21. The method of claim 14 comprising measuring hydrogen ion, oxygen, or carbon dioxide concentration change using a sensor disposed in contact with said medium.

22. The method of claim 14 comprising measuring hydrogen ion concentration change using a fluorophore having an optical property which changes as a function of hydrogen ion concentration.

* * * * *